United States Patent [19]
Rodkey et al.

[11] Patent Number: 5,428,116
[45] Date of Patent: Jun. 27, 1995

[54] SYNTHESIS OF COMPLEX POLYAMINES FOR AMPHOLYTE PRODUCTION

[75] Inventors: L. Scott Rodkey, Houston, Tex.; Philip R. DeShong, Silver Spring, Md.

[73] Assignee: Board of Regents, The University of Texas System, Austin, Tex.

[21] Appl. No.: 212,588

[22] Filed: Mar. 11, 1994

Related U.S. Application Data

[62] Division of Ser. No. 662,297, Feb. 27, 1991, Pat. No. 5,322,906.

[51] Int. Cl.$^6$ ............... C08G 69/26; C08L 77/00
[52] U.S. Cl. ............... 525/420; 525/54.1; 525/54.11; 525/421; 528/229; 528/324; 528/332; 528/339.5; 514/13; 514/14; 514/15; 514/16; 514/17; 514/18; 514/19; 564/133; 564/134; 564/135; 564/137; 564/152; 564/153; 564/511; 564/512
[58] Field of Search ............... 564/511, 512, 153, 152, 564/133, 134, 135, 137; 514/13, 14, 15, 16, 17, 18, 19; 528/229, 324, 332, 339.5; 525/54.1, 54.11, 420, 421

[56] References Cited

U.S. PATENT DOCUMENTS 3,485,736  12/1969  Vesterberg ............ 204/180
4,131,534  12/1978  Just ............ 560/205

OTHER PUBLICATIONS

The Merck Index, An Encyclopedia of Chemicals, Drugs and Biologicals, 11th Ed., published by Merck & Co., Inc., Rahway, N.J., 1989, pp. 127, 2604, 5133, 5586.

*Primary Examiner*—John Kight, III
*Assistant Examiner*—P. Hampton-Hightower
*Attorney, Agent, or Firm*—Arnold, White & Durkee

[57] ABSTRACT

New synthesis and analysis procedures for novel crosslinked polyamines and ampholytes. Polyamines are crosslinked with tartaric acid ester, malonic acid ester, or polycarboxylic acid esters of the citric acid cycle. The resulting crosslinked polyamine may further react with other compounds such as an $\alpha,\beta$-unsaturated or $\alpha$-halo unsaturated carboxylic acids to prepare new ampholyte mixtures. The resulting novel ampholytes exhibit greater heterogeneity and complexity than presently prepared ampholytes, and can be used in analytical and preparative isoelectric focusing processes.

Novel ampholyte analysis process entails analyzing chemical compounds, usually ampholytes, used in isoelectric focusing processes. The ampholyte is isoelectrically focused on an immobilized pH gradient, and then immersed in a picric acid solution to cause precipitation and visualization of amphoteric species. The isoelectrically focused and visualized ampholyte compounds may be photographed or analyzed densitometrically to compare it with other isoelectrically focused and visualized ampholytes to determine relative heterogeneity of the ampholytes over given pH ranges.

25 Claims, 3 Drawing Sheets

SYNTHESIS OF COMPLEX POLYAMINES FOR AMPHOLYTE PRODUCTION

This is a divisional of application Ser. No. 07/662,297 filed Feb. 27, 1991, since issues as U.S. Pat. No. 5,322,906, Jun. 21, 1994

BACKGROUND OF THE INVENTION

1. Field of the Invention

The present invention is concerned with a new synthesis procedure for preparing novel crosslinked polyamines. The crosslinked polyamines may be used to synthesize new zwitterionic compounds suitable for use as ampholytes in isoelectric focusing of amphoteric substances.

In addition, this invention relates generally to the field of chemical compound analysis. More specifically, a method is described for analysis of carrier ampholytes used in isoelectric focusing. The method includes focusing carrier ampholytes on immobilized ph gradients and then visualizing the ampholytes by precipitation using precipitating solutions such as picric acid.

2. Description of the Related Art

1. Ampholyte Synthesis

Isoelectric focusing ("IEF") is a known process for resolving individual molecular species under either denaturing or non-denaturing conditions. IEF is used to separate, purify, and analyze amphoteric substances such as proteins, enzymes, hormones, antigens, antibodies, etc. IEF is a process wherein an applied electrical field forces heterogeneous carrier zwitterions, zwitterionic mixtures, or ampholytes to segregate into an ordered array of molecules, thus establishing a pH gradient between the anode and cathode electrodes. This procedure can be carried out in either a free solution format or in a gel format.

A zwitterion is a molecule that has at least one region of positive charge and at least one region of negative charge. Ampholytes are substances that may ionize to form either anions or cations. Ampholytes may comprise zwitterions and vice versa. Preferentially, ampholytes used in this invention comprise a mixture of numerous species of zwitterionic chemicals which differ from each other by the nature and number of basic and acidic groups.

Each ampholyte species in an ampholyte mixture has its own intrinsic isoelectric point. In a particularly suitable system of carrier ampholytes, the isoelectric points of the different ampholyte species will cover the pH range 3–10. Most naturally occurring proteins, enzymes, hormones, antigens, antibodies, etc. are isoelectric at some point within this pH range. Substantially uniform distribution of the inherent isoelectric points of the various ampholyte species throughout the desired pH range is an important factor for the formation of uniform and linear pH gradients.

U.S. Pat. Nos. 4,131,534 to Just, 3,901,780 to Denckla, 3,692,654 to Svendsen, and 3,485,736 to Vesterberg all outline various methods for preparing carrier ampholytes.

One well-known method of preparing carrier ampholytes involves synthesizing polyamine-polycarboxylic acid mixtures for use as carrier ampholytes. This method typically utilizes a polyethylene polyamine to which an $\alpha,\beta$-unsaturated acid such as acrylic acid is chemically linked by an addition reaction. The simplest ampholyte formed by that reaction is a polyethylene polyamine molecule to which one carboxylic acid molecule is linked, forming a $\beta$-amino carboxylic acid system. Because multiple amino groups are present in the molecule, the addition reaction can occur more than once. Subsequent addition reactions yield $\beta$-amino polycarboxylic acids which contain an increasing number of carboxylic acids in the molecule.

As a result of the above synthesis, some of the resulting ampholyte species are obtained in a high yield whereas other species will be formed at the same time in relatively low yield. A suitable ampholyte mixture should preferably exhibit a uniform distribution of buffering capacity and conductivity throughout the pH gradient and preferably provide a large number of buffering species per pH unit. The ampholyte mixture should preferably be evenly distributed across the pH span. The preferable conditions may be achieved when the different ampholyte species are contained in the mixture in approximately equal concentrations. Therefore, at the end of the chemical reaction, fractionation of the ampholyte mixture in expensive multicompartment electrolysis equipment is normally necessary to blend acceptable mixtures by boosting the concentrations of species obtained at low yield in the initial synthesis. A useful ampholyte mixture is then obtained by mixing appropriate amounts of materials from different electrolysis compartments.

The above method of synthesis makes use of known organic chemistry procedures. There are numerous examples in the literature in which nucleophilic substances (such as the amino groups here) react with electron-deficient alkenes (i.e. acrylic acid) to afford addition products. In these instances, it has been demonstrated that the addition reaction yields favorable results when equimolar quantities of each reactant are utilized.

The above method of synthesis involves adding a calibrated amount of aqueous unsaturated carboxylic acid to an aqueous solution of polyethylene polyamine, with simultaneous heating and stirring. Instead of a single amine, amine mixtures may be used. Similarly, instead of a single carboxylic acid, a mixture of several carboxylic acids each containing at least one carbon-carbon double bond within their molecules may be utilized.

Since the reaction between the unsaturated carboxylic acid and the polyethylene polyamine exhibits slow reaction kinetics at room temperature, the reaction is generally performed at elevated temperature. This procedure, however, leads to undesired side products which cause coloration of the product. Additionally, even at elevated temperature, the reaction kinetics are rather slow and it takes several hours for all of the unsaturated carboxylic acid to react.

A problem with the prior art synthesis of carrier ampholyte mixtures is that the starting polyethylene polyamine compounds which are commercially available come in only a limited number of straight chain forms. Thus, the number of different molecular species or isomers of ampholytes that can be made from these is quite limited. Because of all of the above problems, known procedures are not completely satisfactory, and persons skilled in the art have searched for improvements.

2. Ampholyte Analysis

The resolving power of IEF is largely dependent upon the nature of the pH gradient used. Ideally, the pH gradient should be stepless with an even distribution of charged groups throughout the pH range of interest. Immobilized pH gradients ("IPGs") have overcome many of the problems associated with the uneven distribution of charged groups. However, IPGs are generally limited to analytical and small scale preparative procedures using polyacrylamide matrices. In certain applications IPG analysis requires carrier ampholytes to avoid protein-matrix interactions.

In contrast to IPGs, carrier ampholytes ("CA") have the advantage of being used with virtually any IEF support medium (polyacrylamide, agarose, Sephadex, etc.) or with liquid phase preparative equipment. The resolution of a CA gradient is dependent upon the number and quality of the ampholyte species which are used to generate it. The distribution of ampholyte species over a given pH range becomes especially important when considering narrow range preparative or analytical procedures. For research efforts which are aimed at producing more diverse ampholytes it is preferable to have a reproducible method for monitoring the approximate number and linear charge distribution of the ampholyte species which have been synthesized.

Attempts to estimate the total number of molecular species in ampholyte preparations have met with criticism. Some practitioners have emphasized that the absolute number of molecular species in an ampholyte preparation is of limited importance as compared to the buffering capacity of the species which are present. Nevertheless, such methods have been helpful for evaluating the relative heterogeneity of ampholyte species.

One method of estimating the total number of molecular species involves focusing ampholytes in Sephadex (Pharmacia-LKB Biotechnology [LKB], Bromma, Sweden), then rolling a sheet of filter paper saturated with 5% glucose onto the gel surface. The filter paper is then removed and heated at 110° C. to produce visible ampholyte-glucose caramel reaction products. Using this technique, it was estimated that LKB wide range Ampholines contain approximately 62 carrier species. In another method, a paper print of focused ampholytes is treated with formaldehyde, lactose, or ninhydrin. Using this method, wide range LKB Ampholines have been estimated to comprise more than 500 individual species. Discontinuities in ampholyte distribution have been detected by Schlieren patterns and side illumination of focused gels.

Carrier ampholyte heterogeneity has also been studied using methods which attempted to estimate the distribution of conductivity, and the ability of ampholyte preparations to resolve focused proteins. Although the last approach may be the most direct for choosing an ampholyte mixture for separation of specific groups of proteins, its broad application is limited by the lack of a suitable protein preparation which contains a continuum of closely spaced, well-defined protein species.

All of the above-mentioned analytical methods rely on conventional IEF in gradients which are generated by the ampholytes themselves. In contrast, IPG analysis separates ampholytes in a gradient which is dictated by a smooth and continuous distribution of charged groups covalently bound on a gel matrix. Individual ampholyte species migrate to a position in the pH continuum of the IPG which is indicative of their pI.

Prior to this invention, no method known to the inventors has been developed to analyze ampholytes using a constant calibrated medium to compare the heterogeneity of different ampholyte compounds.

SUMMARY OF THE INVENTION

1. Ampholyte Synthesis

A general object of this invention is to make more complex and heterogeneous polyamine mixtures. These mixtures can then be used to prepare ampholytes of greater complexity and therefore, greater resolution. The ampholytes of this invention may be used for either analytical or preparative purposes.

One advantage of using crosslinked polyamines for making ampholytes is that the resulting ampholytes may be fractionated to prepare narrow pH gradients. Because the novel ampholytes are more heterogeneous and complex than previous ampholytes, better resolution of molecules that have similar isoelectric points is possible.

One reason that commercially available ampholytes lack heterogeneity is that the commercially available polyamine starting materials are available in only a limited number of straight chain forms [e.g., diethylenetriamine (DETA). triethylenetetramine (TETA), tetraethylenepentamine (TEPA), and pentaethylenehexamine (PEHA)]. Thus the number of ampholyte species created is correspondingly limited. The present invention approaches this problem by crosslinking polyamines to generate larger polyamines with highly complex isomeric forms.

An advantage of the present invention is that the crosslinking compounds do not add ionically charged groups to the polyamines during the reaction. Adding ionically charged groups to the polyamines could be detrimental to subsequent synthesis of ampholytes, since preferably ampholytes are synthesized in a basic pH environment.

Another advantage of this invention is that the reactions proceed quickly and efficiently.

Generally, a first aspect of this invention includes preparing a crosslinked polyamine compound, comprising the reaction product of a polyamine and a crosslinking reactant, wherein the crosslinking reactant is a tartaric acid ester (such as diethyltartaric acid ester ("diethyl tartrate")), a malonic acid ester, a polycarboxylic acid ester of the citric acid cycle, or mixtures thereof. A second aspect of this invention includes preparing an ampholyte mixture, comprising the reaction product of a crosslinked polyamine compound and an $\alpha,\beta$-unsaturated carboxylic acid such as acrylic acid.

2. Ampholyte Analysis

Once an ampholyte mixture is prepared, it is desirable to analyze it to determine its heterogeneity. The ampholyte analysis aspect of this invention uses IPGs for the separation and subsequent analysis of ampholyte heterogeneity and distribution. Under these conditions the pH gradient is dictated by the immobilized groups. Typically, a gel containing the immobilized pH gradient is washed, prefocused, and cut into strips prior to application of an ampholyte to the gradient. Upon application, the ampholyte is itself focused to separate the various ampholyte species. The individual ampholyte species, during IEF, migrate to their individual isoelectric points. The gel is then immersed in a solution containing chemicals which cause in situ precipitation of the separated ampholyte species. A saturated solution of picric acid is preferably used to precipitate the ampholyte species so that they can be detected. The different species appear as distinct bands, each separate band indicating the presence of at least one distinct ampholyte species. The bands may be photographed for comparative or archival purposes or they may be scanned in a densitometer for quantitation of the relative content of ampholytes found in individual bands.

Using this invention, significant variations between different commercial sources of ampholytes, as well as ampholytes synthesized in the laboratory, are apparent. An ampholyte that contains fewer molecular species exhibits only a limited number of bands and an ampholyte containing a large number of molecular species exhibits numerous bands. Thus, one advantage of this invention is that it provides a relatively quick, simple, and inexpensive method of analyzing chemical compound heterogeneity, especially ampholyte heterogeneity.

Another advantage of this invention is that a reproducible immobilized pH gradient system is used to analyze the ampholytes. The pH gradient is immobile and reproducible because the chemicals which generate the gradient may be obtained in a highly purified state, may be accurately weighed, and are coupled covalently to the acrylamide gel matrix during polymerization of the gel. Thus, the position in the gel where the individual ampholyte molecules migrate in an electrical field is not dictated by the ampholyte mixture itself, but instead is dictated by the commercially available and reproducible immobilized pH gradient. In effect, this invention provides a method to create an independent pH gradient for separation and eventual visual or quantitative analysis of ampholytes.

This invention may be used to help create ampholytes with improved properties. As is shown in the preferred embodiment, a relationship exists between ampholyte heterogeneity as demonstrated by this invention and the resolution of proteins in IPGs. Since the immobilized pH gradient is constant and reproducible, testing of different ampholyte compounds using this invention enables practitioners to compare ampholytes. Thus, a practitioner can analyze two different ampholytes on the same immobilized pH gradient and compare them to one another (or to a previous standard) for the degree of heterogeneity. Therefore, commercially available immobilized pH gradients may be used as a "standard" for testing ampholytes.

A practitioner may also use the invention described in this disclosure to select and test synthesized and commercial ampholytes for specific applications. For instance, using this invention a practitioner may be able to test and select an ampholyte that exhibits greater resolution in one narrow pH range and a second ampholyte that exhibits greater resolution in a different narrow pH range.

DESCRIPTION OF PREFERRED EMBODIMENTS

1. Ampholyte Synthesis

A first aspect of this invention comprises crosslinking polyamines with reactants such as tartaric acid ester, malonic acid ester, or carboxylic acid esters of the citric acid cycle. These acid esters may be in the L, D, meso, or racemic form. For instance, L-diethyltartaric acid ester, D-diethyltartaric acid ester, meso-diethyltartaric acid ester, or racemic diethyltartaric acid ester may be used. In addition, the alkyl portion of the esters may be replaced with other alkyl radicals (other than ethyl) such as methyl, propyl, or isopropyl radicals. The esters, when added to a polyamine compound in the presence of heat without oxygen, crosslink the polyamine compounds, creating a large number of heterogenous polyamine crosslinked isomers.

In a second aspect of the invention the crosslinked polyamine compounds are reacted with an unsaturated carboxylic acid to form heterogenous ampholyte mixtures. Thus, crosslinked polyamines may be reacted with an $\alpha,\beta$-unsaturated carboxylic acid such as acrylic acid to form an ampholyte mixture. Other suitable $\alpha,\beta$-unsaturated carboxylic acids comprise methacrylic acid, methylene malonic acid, ethylene malonic acid, crotonic acid, maleic acid, fumaric acid, itaconic acid, or mixtures thereof. The resulting ampholyte may be diluted with water and cooled, or otherwise allowed to cool, to ambient temperatures. Samples of the resulting ampholytes may be isoelectrically focused on an IPG, precipitated, and photographed for analytical purposes. The ampholyte may be subsequently used as a carrier ampholyte to separate amphoteric substances such as proteins, enzymes, antibodies, antigens, hormones, etc.

In all reactions contemplated, polyamine mixtures may be used instead of a single polyamine. Furthermore, a mixture of crosslinking reactants comprising tartaric acid ester, malonic acid ester, or a polycarboxylic acid ester of the citric acid cycle may be utilized. Mixtures of any of the reactants in the subject invention may be used to provide for a more heterogenous ampholyte mixture.

A particular advantage of the present invention is that it may use commercially available polyamines, crosslinking reactants, and $\alpha,\beta$-unsaturated carboxylic acids. All of these compounds are relatively inexpensive and are available in an acceptable purity grade.

Polyamine compounds which are employed for the synthesis of carrier ampholytes will in most embodiments contain at least two amino or imino groups. Most polyamines which are suitable for the present procedure will comprise the following unit: —NH—R— NH—. In addition, it is anticipated that some polyamines may also comprise peptides.

The chain length (—NH—R—NH—) of the polyamine may be prolonged in both directions with similar —R—NH— units. For special purposes, resulting compounds may have molecular weights of 20,000 or more. In the above formula, R may be —$C_3H_6$—, —$CH_2$—, or preferably —$C_2H_4$—. Typically, the organic nitrogen compounds will be linear chain molecules. Moreover, various nitrogen atoms may be substituted by alkyl groups which may contain 1-6 carbon atoms. Preferred polyamines are polyethylene polyamines such as DETA, TETA, TEPA, and PEHA.

In addition to the above polyamines, it is contemplated that other polyamines such as peptides may be used. It is envisioned that most useful peptides will comprise at least two amino groups and a chain of 3-20 amino acids, preferably 3-10 amino acids. A chain length of 3-10 amino acids is preferred due to the relatively low molecular weight of the final product. The lower molecular weight generally makes it easier to separate the resulting ampholyte from the larger amphoteric protein molecules after IEF. Examples of peptides that are contemplated to be useful as polyamines include peptides comprising basic amino acids such as L-lysine, D-lysine, L-arginine, D-arginine, L-histidine, D-histidine, or mixtures thereof. In addition, mixtures of different peptides comprised of different sequences of amino acids are also contemplated. Thus, one peptide comprised of a particular sequence of amino acids may be mixed with one or more peptides comprised of different sequences of amino acids. Varying chain length peptides may also be mixed.

Peptide polyamines outlined above may be mixed with other polyamines such as polyethylene polyamines to achieve a more heterogeneous mixture of starting polyamine. The more complex and heterogeneous the starting polyamine, the more likely the resulting ampholyte mixture will be complex and heterogeneous, thus increasing the resolution potential of an ampholyte mixture.

The preferred crosslinking reactants comprise tartaric acid ester, malonic acid ester, and carboxylic acid esters of the citric acid cycle. The citric acid cycle is a well-known biological chemical reaction sequence, and it is contemplated that suitable carboxylic acid esters from that cycle include maleic acid ester, oxaloacetic acid ester, citric acid ester, aconitic acid ester, isocitric acid ester, oxalosuccinic acid ester, and $\alpha$-ketoglutaric acid ester.

Hydroxyl groups present in most of the above-named esters impart two properties to the resulting crosslinked polyamine. First, the presence of hydroxyl groups increases the water solubility of the crosslinked polyamine by making it more hydrophilic. Second, the hydroxyl groups serve as hydrogen-bonding acceptors and donors. Most biological molecules (i.e. enzymes, proteins, antibodies, antigens, etc.) depend heavily upon hydrogen-bonding for the maintenance of their three-dimensional integrity. The ability of the crosslinked polyamines to participate in hydrogen-bonding generally results in increased interaction between the molecules to be purified or analyzed, and the ampholytes prepared from the crosslinked polyamines. Thus, the resulting ampholytes, because of the hydrogen-bonding properties of the crosslinking reactants, exhibit improved separations.

In one embodiment, the unsaturated acid monomers which are used in the invention contain a carbon-carbon double bond activated for addition to the amino group. Carboxylic acids with a double bond in the $\alpha,\beta$-position are preferably used although the double bond may be positioned elsewhere within the molecule and the molecule may be activated otherwise.

For the controlled synthesis of an ampholyte mixture, gradual mixing of the starting materials is employed. Heating the reactants in an oxygen-free atmosphere such as an inert gas (nitrogen) is part of the synthesis process. The mixing ratios of the two reactants may be calculated with accuracy from the molecular weights of the reactants. For example, since each acrylic acid molecule has one amino-reactive group and each PEHA molecule has two primary amino groups and four secondary amino groups, it is predictable that even at total saturation only a maximum of eight acrylic acid molecules could couple to each PEHA molecule. Obviously, any number less than eight acrylic acid molecules could couple to each molecule of PEHA on average.

In practice, approximately one mole of $\alpha,\beta$-unsaturated acid is reacted for every two available primary or secondary amino groups to make an acceptable ampholyte with a pH range from 3-10. Thus, for example, for every mole of PEHA, which has six available amino groups, three moles of acrylic acid is required to react with the PEHA to make a pH 3-10 ampholyte mixture. "Available" amino groups should be interpreted to mean primary or secondary amino groups. If two moles of PEHA are crosslinked with diethyltartaric acid ester, then only ten amino groups are available and therefore five moles of acrylic acid are theoretically required.

The present procedure produces a carrier ampholyte mixture which may have a slight yellow-brown coloration. To remove that coloration and to lower absorption in the ultraviolet region of the spectrum, the carrier ampholyte mixture may be treated with hydrogen in the presence of a suitable catalyst. Raney-nickel, platinum oxide, palladium, palladium-activated carbon, or hydrides such as lithium aluminum hydride and sodium borohydride may be used. The hydrogenation is preferably performed in aqueous solution but may also be carried out in a suitable organic solvent. In addition, activated charcoal chromatography may also be used for decolorization.

One preferred embodiment was prepared as follows. A crosslinked polyamine compound was prepared by adding diethyltartaric acid ester with a polyamine in a tetrahydrofuran solvent solution. Other solvents that may work acceptably in this application include ether, dioxane and benzene. The diethyltartaric acid ester was added dropwise while stirring the mixture. The diethyltartaric acid ester and the polyamine were added in substantially equal molar quantities and heated at reflux for approximately 6 hours. The atmosphere of the reaction vessel was flushed with anhydrous oxygen-free gas (nitrogen gas), and the vessel was sealed and heated at approximately 50° C. for approximately 12-16 hours. Methane, any other hydrocarbon gas, or any of the inert noble gases (helium, neon, argon, krypton, xenon) may also be used as an oxygen-free atmosphere for this invention. Following heating, the tetrahydrofuran solvent was removed by evaporation in a partial vacuum of around 30 mm Hg. The result was a complexed crosslinked polyamine compound.

Following synthesis of the crosslinked polyamine compound, that compound may be stored or used to synthesize an ampholyte. If an ampholyte is to be prepared, the crosslinked polyamine compound is diluted with water and mixed with an appropriate amount of $\alpha,\beta$-unsaturated carboxylic acid. It is well understood to persons skilled in the art that water may be added in varying amounts to achieve desired compound concentrations. The $\alpha,\beta$-unsaturated carboxylic acid used in one preferred embodiment was acrylic acid and the polyamine compound was first cooled to a temperature of about 25°-30° C.

After adding acrylic acid in the above examples, the atmosphere of the vessel was once again flushed with an oxygen-free atmosphere and the vessel was then sealed and heated to approximately 70° C., with stirring, for approximately 16 hours. Water was then added to bring the ampholyte solution to a final concentration of 40% (weight/volume). This is a generally appropriate concentration although any other concentration is acceptable.

The polyamine compound may be a mixture of various polyamines. In addition, the relative amount of tartaric acid ester may be varied. In one preferred embodiment, a molar ratio of 3:4 (tartaric acid ester:polyamine) was used. Similarly, the molar ratios of available polyamine amino groups to unsaturated $\alpha,\beta$-unsaturated carboxylic acid may also be varied. A molar ratio of 2:1 (available polyamine amino: $\alpha,\beta$-unsaturated carboxylic acid) yielded optimal ampholytes with the mixtures utilized. It will be understood by those skilled in the art that the molar ratios may be varied to prepare different complexed polyamine mixtures.

Similarly, it will also be understood that the temperatures and times of the reactions of the invention may also be varied. It is contemplated, for example, that the crosslinking reaction may take place within a temperature range of 30°–140° C., preferably 40°–60° C. and for a period of 2–48 hours, preferably 12–20 hours. When an unsaturated carboxylic acid is added to the crosslinked reactant, that reaction may take place at a temperature range of 50°–140° C., preferably 60°–80° C., and a time period of 2–48 hours, preferably 12–20 hours. It is anticipated that higher temperatures will normally require less reaction time and vice versa.

Figure 1:
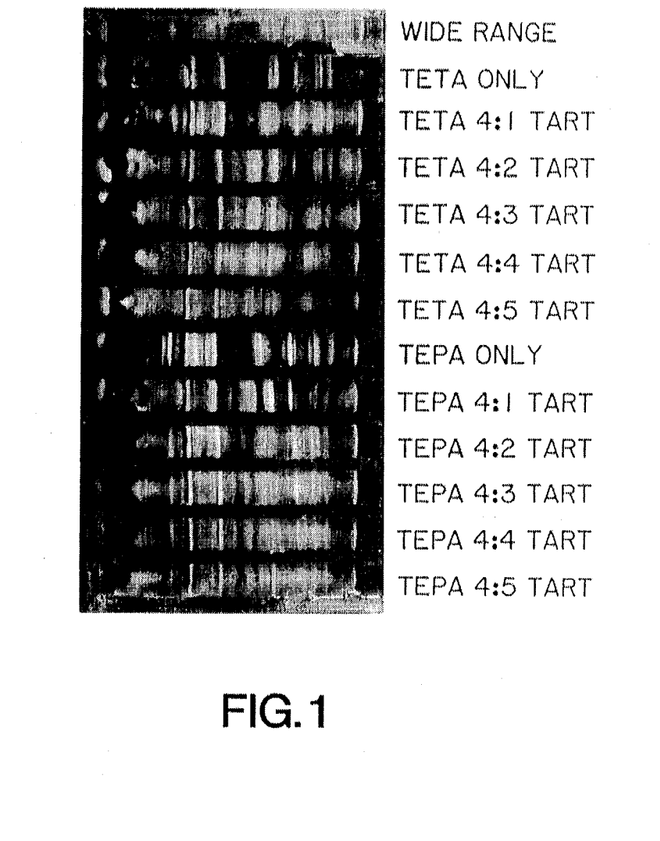
FIG. 1 is a photograph of several synthesized TETA and TEPA derivative ampholytes visualized on immobilized pH gradients.
Figure 2:
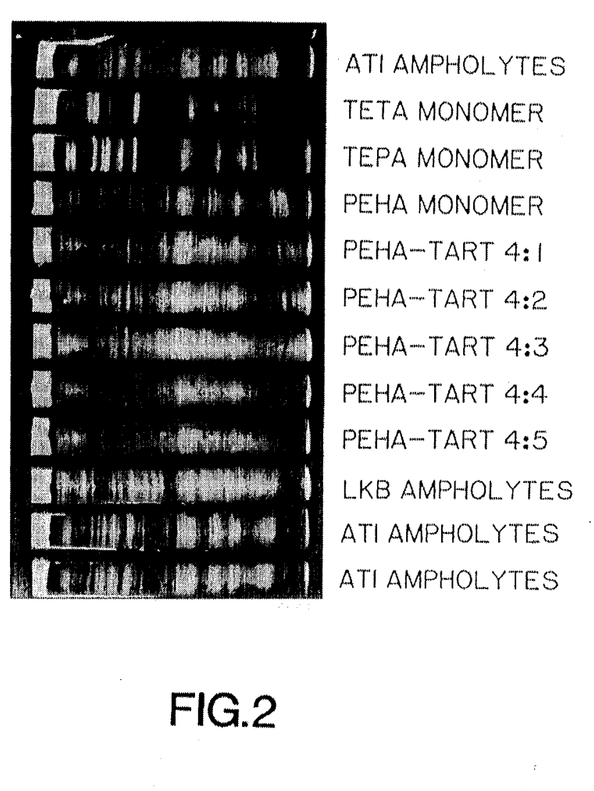
FIG. 2 is a photograph of several synthesized and several commercial ampholytes visualized on immobilized pH gradients.

TETA, TEPA, and PEHA were all crosslinked in molar ratios of 4:1, 4:2, 4:3, 4:4, and 4:5 of polyamine to L-diethyltartaric acid ester. A 2:1 ratio of available crosslinked polyamine amino groups to acrylic acid was subsequently utilized to synthesize ampholytes. The ampholytes were then isoelectrically focused and analyzed using commercial solid state pH gradient media (LKB). The analysis was completed according to the process described below in the "Ampholyte Analysis" section herein. For comparative purposes, ampholytes synthesized from TETA, TEPA, and PEHA monomers were also visualized, along with commercial ampholytes such as ATI (Ampholife Technologies, Inc., The Woodlands, Tex.) and LKB ampholytes. FIGS. 1 and 2 show the analysis of ampholytes using the methods described. Visual inspection of the patterns is a qualitative method of comparing the ampholytes and provides a rapid method of analysis to assess success or failure in modifying protocols for ampholyte synthesis, but is not necessary to create improved ampholytes as described herein. When quantitative results are desired, the distribution of precipitated bands in the gels can be analyzed using densitometric measurement. One densitometer that may be used is the "Quick Scan Jr." made by Helena Laboratories (Beaumont, Tex.).

The number of regions (in this case, bands) of precipitate seen on the gels gives a minimum estimate of the number of isoelectrically focused ampholyte species. In general, larger numbers of bands in the gel correspond to more heterogeneous and complex ampholytes (a favored result).

As is readily apparent from FIGS. 1 and 2, the ampholytes that were synthesized using the crosslinking reactant (tartaric acid ester) were significantly more heterogenous and complex than the ampholytes made from TETA, TEPA, and PEHA monomers. In addition, some of the PEHA ampholytes that were crosslinked with tartaric acid ester exhibited greater heterogeneity and complexity than commercially available ATI and LKB ampholytes. Since some of the new ampholytes are more heterogeneous and complex than existing commercially available ampholytes, it is envisioned that still other new ampholytes will achieve correspondingly higher resolutions. For instance, different polyamine starting materials such as peptides or peptide-polyethylene polyamine mixtures are contemplated. In like manner, alternate crosslinking reactants (some of which are identified herein) may be utilized.

In addition to having a greater number of ampholyte species, many of the ampholytes made by using crosslinked polyamines are more evenly distributed over the pH range and lack the dominant species which were detected in some preparations. These dominant species may contribute to uneven conductivity when the ampholytes are used for conventional IEF.

It is envisioned that all or portions (corresponding to narrower pH ranges) of the new ampholytes may be used to achieve improved separations of amphoteric substances. In addition, the process of crosslinking polyamines as described in this invention will serve as a useful method for making other novel improved ampholytes. Thus, other ampholyte synthesis processes such as already described in the art may be combined with the crosslinking procedures of this invention to prepare improved ampholytes.

2. Ampholyte Analysis a. Ampholytes

Figure 3:
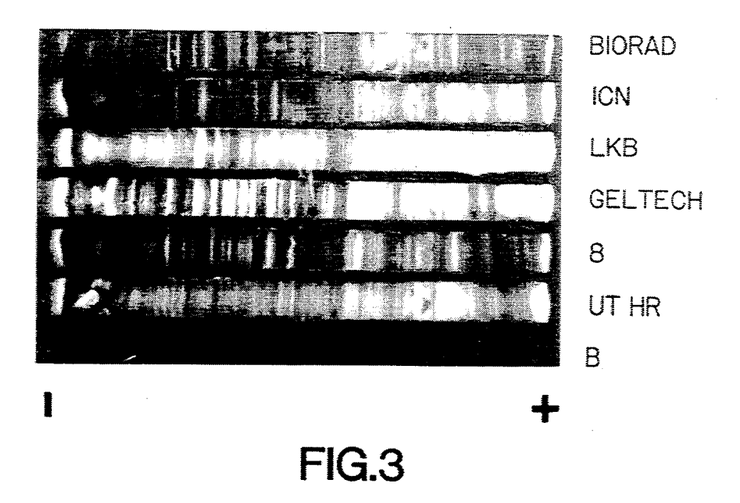
FIG. 3 is a photograph of the results of IPG picric acid analysis of several commercial ampholytes.
Figure 4:
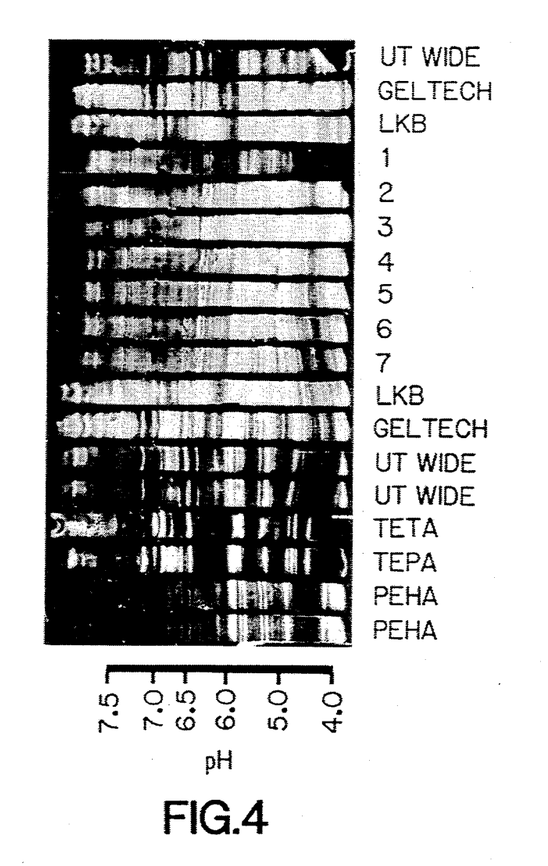
FIG. 4 is a photograph of the results of IPG picric acid analysis of several synthetic and commercial ampholytes.
Figure 6:
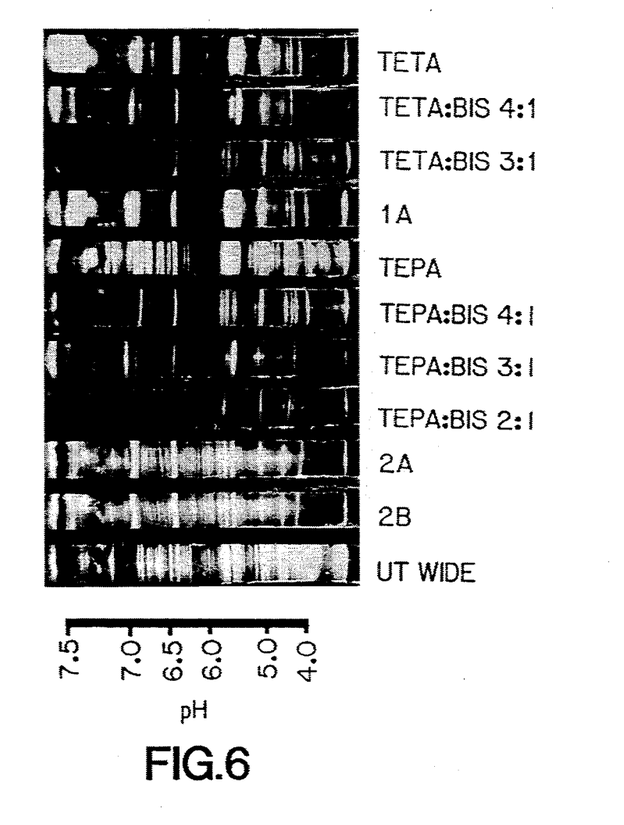
FIG. 6 is a photograph of the results of IPG picric acid analysis of ampholytes synthesized with bis-acrylamide crosslinked polyamines.

Commercial ampholytes were obtained from Bio-Rad (Biolytes, pH 3–10), ICN (Iso-Lytes, pH 3–10), Geltech (Technolytes, pH 3.5–9.5) and LKB (Ampholines, pH 3.5–9.5). Ampholytes 1-1A, 2A and 2B as shown in FIGS. 3, 4, and 6 were obtained from ATI. TETA, TEPA, and PEHA ampholytes were synthesized as described by Binion and Rodkey in *Electrophoresis* 3, 284 (1982) using a 2:1 ratio of available polyamine nitrogen to acrylic acid. A group of ampholytes termed "UT WIDE" ampholytes were prepared by mixing ampholytes made with TEPA and PEHA monomers.

For production of ampholytes using bis-acrylamide crosslinked polyamine, TETA or TEPA were combined with N,N'-methylene bis-acrylamide ("bis") at varying molar ratios and mixed at room temperature overnight. Ampholytes were then synthesized using acrylic acid as previously described (see the well-known method outlined in the "Description of the Prior Art" section). The ampholytes described herein are illustrative examples and in no way limit the scope of the invention. Other chemical compounds or compositions may also be analyzed using this invention, including chemical compounds that are not ampholytes. It is understood that "chemical compound" as interpreted within the context of the claims may be interpreted to mean one chemical compound or a mixture of chemical compounds. The chemical compounds should generally have a pI within the pH range of the immobilized pH gradient. The compounds analyzed should also precipitate, to some degree, when contacted with a chemical precipitating solution (such as picric acid) after IEF on IPGs.

Of course, other ampholytes will also be used in this invention. For example, ampholytes may be preferentially prepared according to the procedures outlined herein (see sections entitled "Ampholyte Synthesis").

b. IPG Analysis of Ampholytes

Polyacrylamide gels ($25 \times 12 \times 0.5$ cm) comprising 4.9% T, 3% C, and Immobiline chemicals (LKB) were used for the production of pH 4-10 gradients according to the gel formulations described by Fawcett and Chrambach. See *Prot. Biol. Fluids*, 33, 439 (1985). It is anticipated that gels comprising a total acrylamide concentration ("T") of 1-10% (3-7% preferred), and a percentage crosslinker of T ("C") of 1-5% (2-4% preferred) may be used for this invention. In general, the higher the percentage of C, the tighter the gels are bound together.

In general, the IPGs comprise acrylamide derivatives, with the formula $CH_2=CH-CO-NH-R$, where R denotes one of several possible ionizable groups, with pK's in the pH 3.6-9.3 range. In general R may be 2-acrylamido-2-methylpropane, 2-acrylamido glycolic acid, N-acryloyl glycine, 3-acrylamido propanoic acid, 4-acrylamido butyric acid, 2-morpholino ethylacrylamide, 3-morpholino propylacrylamide, N,N-dimethyl aminoethyl acrylamide, N,N-dimethyl aminopropylacrylamide, N,N-diethyaminopropylacrylamide, QAE-acrylamide (quaternary aminoethyl acrylamide), or mixtures thereof.

IPGs are generally prepared by using nonamphoteric weak acids and bases coupled to an acrylamide backbone, mixed in such ratios as to define any desired pH interval. The weak acids and bases are incorporated as a gradient of charges (and thus immobilized) into the supporting polyacrylamide matrix using a commercially available gradient making device. The formula of IPG compounds and their synthetic routes are reported in "Synthesis of Buffers for Generating Immobilized pH gradients. I: Acidic acrylamido buffers," *Applied and Theoretical Electrophoresis* 1, 99-102 (1989) and "Synthesis of Buffers for Generating Immobilized pH gradients. II: Basic Acrylamido Buffers," *Applied and Theoretical Electrophoresis* 1, 103-108 (1989). It is envisioned that this invention will be applicable to most types of IPGs, and not limited to the IPGs described herein. For instance, discovery of additional chemicals which would extend the resulting IPG acid range lower or the IPG basic range higher than the IPG chemicals described above would also be applicable IPG examples as would the discovery of chemicals which could replace the chemicals described above in their respective pI ranges. Commercial brand LKB chemicals as described above were preferred.

In this embodiment, the gels were polymerized, washed in distilled water, washed with 1% glycerol, and dried for storage. Before running, the dried gels were hydrated for 2 h in distilled water and prefocused overnight at 0.5 W limiting power at 8° C. to remove any residual catalysts remaining from the acrylamide polymerization (ammonium persulfate and tetramethylethylenediamine) and to exude excess liquid from the gel prior to application of the ampholyte samples. The following morning prefocusing was continued for at least 1 h limited at 2.0 W and 5000 V during which time excess fluid was blotted from the gel surface. After prefocusing, 0.5 cm lanes were cut in the gel with approximately 0.2 cm spaces between the lanes. Ampholyte samples were applied to each lane (5 microliters of 4% ampholyte per lane) positioned at approximately 1 cm from the cathode. Focusing was performed for 6 h limited at 5000 V, 0.5 mA and 2.3 W.

Upon completion of the run the gel was immediately immersed in saturated picric acid in water to precipitate the focused ampholytes rendering them visible. "Visualization" is the process whereby the separated species of the analyzed compound become visible on the IPG. The total IPG pH gradient was measured using a flat surface pH electrode on a separate lane of the same gel to which wide range LKB ampholytes had been applied. This lane was removed from the gel for pH analysis before treatment of the remaining gel with picric acid. The resulting visualized ampholytes were aligned and photographed as shown in FIGS. 3-6.

c. Results of IPG Analysis of Commercial and Prepared Ampholytes

In FIG. 3 four commercially available wide range ampholytes and two synthetic preparations were analyzed. Regions (bands) in the pH gradient represent focused ampholyte species which were precipitated in situ with picric acid. All commercially available ampholytes tested (Described in Preferred Embodiment, Section 2a) contained picric acid precipitable ampholyte species across the entire pH range. Therefore, the characteristics of the ampholyte species which render it precipitable with picric acid do not appear to be dependent on the pI of the ampholyte molecule.

IPG picric acid analysis of different synthetic ampholytes and commercial ampholytes (Described in Preferred Embodiment, Section 2a) is shown in FIG. 4. The relative heterogeneity of ampholytes which were synthesized using the polyamine PEHA as a backbone was compared to ampholytes which were synthesized using the polyamines TETA or TEPA as a backbone. The TETA and TEPA patterns consist of relatively few precipitable species, and contain obvious deficiencies in certain areas of the gradient.

PEHA ampholytes produced a more heterogeneous pattern of precipitable species. Dominant species which were present in the TETA and TEPA samples were not detected in the PEHA sample. Furthermore, gaps in the distribution of bands which were detected in the TETA and TEPA preparations were "filled in" in the PEHA sample, providing a more even distribution of ampholytes. Thus, a relationship appears to exist between the relative heterogeneity of picric acid precipitable ampholyte species and theoretically predicted heterogeneity (based on molecular size and the theoretical number of ampholyte species which may be generated). As would be theoretically predicted, ampholytes made from PEHA exhibited greater ampholyte heterogeneity because of the larger number of ampholyte species generated. In addition, any branching of the polyamine, which is more likely with larger polyamines such as PEHA, tends to increase ampholyte heterogeneity.

The method of this invention may be valuable in monitoring the heterogeneity of ampholyte preparations. FIG. 4 shows IPG picric acid analysis patterns of ampholytes obtained wherein the ampholytes were produced using the well-known synthetic procedure previously described. This procedure synthesized ampholytes using unmodified PEHA, TEPA or TETA with one mole acrylic acid for every 2 moles of available polyamine amino group. The FIG. 4 analyses demonstrate that with appropriate manipulation ampholytes may be prepared that have greater diversity than ampholytes prepared with unmodified TETA, TEPA, or PEHA monomers.

The demonstration of a larger number of ampholyte species detected using the polyamine crosslinking method demonstrate that it is possible to synthesize ampholytes which are superior with regard to isoelectric heterogeneity than presently available ampholytes. The larger number of available polyamine isomers available for coupling to the acid molecules increases the overall heterogeneity of the resulting ampholytes. The new ampholytes may have the potential for higher resolution of proteins than less heterogeneous preparations because the larger number of carrier ampholytes per linear distance unit on the IPG will provide a better environment for two protein molecules with very closely-spaced pI to be detected as two distinct bands rather than as one thick band.

d. Relationship of IPG Pattern to Protein Resolution

In designing new ampholyte synthesis procedures, it is important to confirm that the banding pattern obtained by IPG picric acid analysis is indicative of the potential of these ampholytes to resolve proteins when used in conventional IEF. The relationship between ampholyte heterogeneity and resolution of focused proteins is demonstrated in FIG. 5. Serum proteins taken from rabbits during the course of active immunizations were separated by IEF using standard TEPA or PEHA ampholytes made using unmodified TEPA or PEHA for ampholyte synthesis with acrylic acid added at a ratio of one mole of acrylic acid/2 moles of available polyamine amino groups.

Flatbed IEF was performed in LKB Multiphor chambers at 8° C. to analyze the serum proteins. Polyacrylamide gels (25×12×0.5 cm) comprised 5.3% T, 3% C, and 3% ampholyte. Electrode wicks were saturated with 1M NaOH (cathode) and 1M $H_3PO_4$ (anode). Ten microliter samples of serum diluted 1:5 were applied to the gel surface using silicone rubber surface applicators. The IEF protocol began with an initial setting of 100 V (constant voltage) for 15 minutes, and was then raised to 200 V (constant voltage) for an additional 15 minutes. The setting was then switched to 5 W (constant power) for 60 minutes followed by 7 W (constant power) for an additional 30 minutes. The pH gradient was measured immediately following electrophoresis using a flat surface pH electrode. Proteins were fixed (immobilized and preserved) in the gel by placing the gel in a fixative solution consisting of 3.45% sulfosalicylic acid, 11.5% trichloracetic acid in 30% methanol for 1 h with rocking. The gels were then rinsed in 25% ethanol, 8% acetic acid for 1 h, the rinse solution was changed, and a second rinse was done overnight. The gel was then immersed in the same solution containing 0.1% Coomassie Brilliant Blue R250 for 1 h to stain proteins which had been previously fixed so that they could be seen with the naked eye. Gels were destained in order to remove stain from areas of the gel where no protein is located to make the stained areas contrast more vividly with the transparent unstained background gel area. Destaining was done by immersing the gels in several changes of acid alcohol until the backgrounds were clear.

Figure 5:
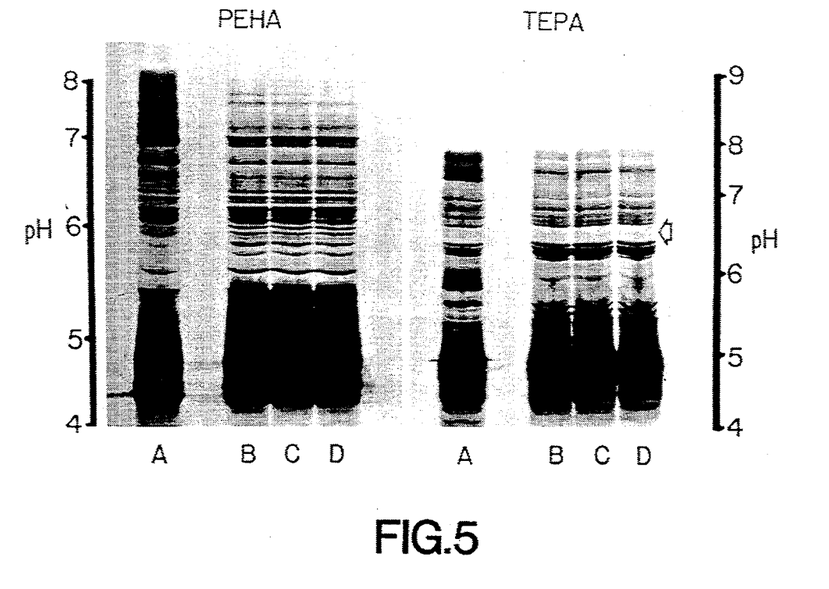
FIG. 5 is a photograph of the results of conventional IEF of serum proteins using ampholytes which were synthesized with tetraethylenepentamine ("TEPA") or pentaethylenehexamine ("PEHA"), and acrylic acid.

As shown in FIG. 5, two major differences between the banding patterns of TEPA and PEHA ampholytes are obvious. First, proteins which were separated in the PEHA gradient are more evenly distributed across the gradient and are therefore more easily resolved than those in the TEPA gel. Second, proteins analyzed by IEF in the TEPA gradient were spread through the gel by obvious gaps (see arrow on FIG. 5) where no protein was detectable. FIG. 5 demonstrates that the fewer the number of ampholyte species, the greater the chance for artifactual grouping of adjacent proteins, resulting in decreased resolution. This grouping is caused when proteins migrating in an area of low buffering artifactually move to the closest available area of buffering. Thus, if there are no buffering species of carrier ampholytes at, for instance, pH 5.2, but there are carrier ampholyte species at pH 5.4, a protein with a pI of 5.2 will move to the pH 5.4 area creating an artifact, or false result. Therefore, a relationship is established between the relative heterogeneity of picric acid precipitable ampholyte species and the potential resolution of proteins in ampholyte gradients.

e. Bis-Acrylamide CrossLinked Polyamines and IPG Precipitation

Picric acid has been previously reported to precipitate all commercially available ampholytes. In the search for synthetic methods to increase ampholyte diversity one method was found which did not produce picric acid precipitable ampholytes. This method involves the use of bis-acrylamide to crosslink the polyamine backbone to create more heterogeneous ampholytes. Picric acid analysis of bis-acrylamide crosslinked ampholytes is shown in FIG. 6. Bis-acrylamide appears to be reacting with both TETA and TEPA in such a way that the resulting ampholyte species are modified. This is clearly demonstrated by the reduction of the major picric acid precipitable species which are evident in the unmodified TETA and TEPA preparations. Under certain conditions (TETA:BIS ratio of 4:1 and TEPA:BIS ratio of 3:1) new species of picric acid precipitable ampholytes were prepared. As the ratio of bis-acrylamide to TEPA increased, the number of picric acid precipitable species decreased.

This aspect of the invention demonstrates the application of IPG ampholyte analysis for new ampholyte syntheses. Polyamine backbones such as TETA or TEPA which produce poor ampholytes have been modified to produce more diverse ampholyte species. The effect of these modifications have been monitored by IPG analysis. Detection of focused ampholyte species in the IPG is dependent upon the formation of a visible complex with picric acid. Picric acid combines with certain amino acids to form picrates and is used routinely in histological fixatives.

Not all ampholytes tested precipitated in picric acid. However, the ampholyte species which did precipitate with picric acid appeared to be distributed across the entire pH gradient, demonstrating that precipitation is not simply a function of the pI of the ampholyte species. A direct correlation has been established between the number and diversity of picric acid precipitable ampholyte species and the potential resolution of focused proteins using these ampholytes in conventional IEF.

The IPG picric acid method of ampholyte analysis allows a qualitative or quantitative comparison of ampholytes which have been produced by various synthetic modifications. The analysis covers a continuous pH spectrum and is not limited by the availability of appropriate pI marker proteins to assess the stepless characteristics of the ampholyte. This method of analysis insures that the ampholytes themselves are not dictating their own distribution patterns. The patterns are dictated by the immobilized pH gradient which is independent of the ampholyte being analyzed. The development of ampholytes with such characteristics may be important in the analysis of protein mixtures such as polyclonal antibody preparations, which are vastly heterogeneous with respect to their isoelectric points. Ampholytes which have many species within a narrow pH range may also be particularly attractive for preparative IEF applications. The potential to expand narrow segments of the pH gradients for preparative IEF applications using narrow range amphoylete fractions isolated by recycling IEF would be more attractive if more species of carrier ampholyte per pH unit were available to separate biomolecules in extremely narrow pH ranges.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein or in the steps or in the sequence of steps of the methods described herein without departing from the spirit and scope of the invention as described in the following claims. Similarly, isomers and homologs of reactants may be used and still come within the scope of the invention.

What is claimed is:

1. A crosslinked polyamine compound, comprising the reaction product of polyamine and a crosslinking reactant, wherein the crosslinking reactant is a tartaric acid ester, a malonic acid ester, a saturated polycarboxylic acid ester of the citric acid cycle, or mixtures thereof.

2. An ampholyte mixture, comprising the reaction product of a crosslinked polyamine compound and an $\alpha,\beta$-unsaturated carboxylic acid wherein the crosslinked polyamine compound is a reaction product of a polyamine and a crosslinking reactant.

3. The ampholyte mixture of claim 2 wherein the crosslinking reactant is a tartaric acid ester, a malonic acid ester, a polycarboxylic acid ester of the citric acid cycle, or mixtures thereof.

4. An ampholyte mixture, comprising the reaction product of the crosslinked polyamine compound in claim 1 and an $\alpha,\beta$-unsaturated carboxylic acid.

5. An ampholyte mixture, comprising the reaction of a polyamine crosslinked with diethyltartaric acid ester, and acrylic acid.

6. The ampholyte mixture of claim 2 wherein the polyamine is a peptide with at least two amino groups, a polyethylene polyamine with at least two amino groups, or mixtures thereof.

7. The ampholyte mixture of claim 2 wherein the polyamine comprises a peptide with at least two amino groups.

8. The ampholyte mixture of claim 2 wherein the polyamine comprises a polyamine with at least two amino groups.

9. The ampholyte mixture of claim 7 wherein the peptide is a 3–20 molecule chain of amino acids, or a mixture of 3–20 molecule chains of amino acids.

10. The ampholyte mixture of claim 9 wherein the chain of amino acids is L-lysine, D-lysine, L-arginine, D-arginine, L-histidine, D-histidine, or mixtures thereof.

11. The ampholyte mixture of claim 8 wherein the polyethylene polyamine is diethylenetriamine, triethylenetetramine, tetraethylenepentamine, pentaethylenehexamine, or mixtures thereof.

12. The ampholyte mixture of claim 8 wherein the polyethylene polyamine comprises diethylenetriamine.

13. The ampholyte mixture of claim 8 wherein the polyethylene polyamine comprises triethylenetetramine.

14. The ampholyte mixture of claim 8 wherein the polyethylene polyamine comprises tetraethylenepentamine.

15. The ampholyte mixture of claim 8 wherein the polyethylene polyamine comprises pentaethylenehexamine.

16. The ampholyte mixture of claim 2 wherein the crosslinking reactant comprises a tartaric acid ester.

17. The ampholyte mixture of claim 2 wherein the crosslinking reactant comprises a malonic acid ester.

18. The ampholyte mixture of claim 2 wherein the crosslinking reactant comprises a polycarboxylic acid ester of the citric acid cycle.

19. The ampholyte mixture of claim 16 wherein the tartaric acid ester is L-diethyltartaric acid ester, D-diethyltartaric acid ester, meso diethyltartaric acid ester, racemic diethyltartaric acid ester, or mixtures thereof.

20. The ampholyte mixture of claim 18 wherein the polycarboxylic acid ester of the citric acid cycle is citric acid ester, oxaloacetic acid ester, aconitic acid ester, oxalosuccinic acid ester, $\alpha$-ketoglutaric acid ester, isocitric acid ester, malic acid ester, or mixtures thereof.

21. The ampholyte mixture of claim 2 wherein the $\alpha,\beta$-unsaturated acid is acrylic acid, methacrylic acid, methylene malonic acid, ethylene malonic acid, crotonic acid, maleic acid, fumaric acid, itaconic acid or mixtures thereof.

22. The ampholyte mixture of claim 2 wherein the $\alpha,\beta$-unsaturated acid comprises acrylic acid.

23. The ampholyte mixture of claim 2 wherein the $\alpha,\beta$-unsaturated acid comprises methacrylic acid.

24. An ampholyte mixture, comprising the reaction product of the crosslinked polyamine compound in claim 1 and $\alpha$-bromo acetic acid, $\alpha$-iodo acetic acid, $\alpha$-chloro acetic acid, $\alpha$-bromo propionic acid, $\alpha$-iodo propionic acid, $\alpha$-chloro propionic acid, or mixtures thereof.

25. A process for making a crosslinked polyamine compound, comprising the step of:
mixing a polyamine with a crosslinking reactant, wherein the crosslinking reactant is a tartaric acid ester, a malonic acid ester, a saturated polycarboxylic acid ester of the citric acid cycle, or mixtures thereof.

* * * * *

UNITED STATES PATENT AND TRADEMARK OFFICE
CERTIFICATE OF CORRECTION

PATENT NO.   :   5,428,116

DATED        :   June 27, 1995

INVENTOR(S)  :   L. Scott Rodkey and Philip R. DeShong

It is certified that error appears in the above-identified patent and that said Letters Patent is hereby corrected as shown below:

In claim 5, column 15, line 50, after 'reaction', insert --product-- therefor.

In claim 8, column 15, line 61, after 'comprises a', insert --polyethylene-- therefor.

Signed and Sealed this

Twelfth Day of September, 1995

Attest:

BRUCE LEHMAN

Attesting Officer

Commissioner of Patents and Trademarks